(12) United States Patent
*Hoie

(10) Patent No.: US 6,268,011 B1
(45) Date of Patent: Jul. 31, 2001

(54) COMPOSITION AND ITS USE AS A FOOD SUPPLEMENT OR FOR LOWERING LIPIDS IN SERUM

(75) Inventor: Lars Henrik Hoie, London (GB)

(73) Assignee: Nutri Pharma ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/524,018

(22) Filed: Mar. 13, 2000

Related U.S. Application Data

(63) Continuation of application No. 09/143,120, filed as application No. PCT/IB97/00152 on Feb. 12, 1997, now Pat. No. 6,136,367.

(30) Foreign Application Priority Data

Feb. 29, 1996 (DK) .................................................. 0227/96

(51) Int. Cl.[7] ............................... A23L 1/20; A61K 38/00
(52) U.S. Cl. ........................ 426/634; 426/656; 426/658; 514/2; 514/909
(58) Field of Search ..................................... 426/634, 656, 426/658, 626, 657, 72, 601, 643, 648, 654

(56) References Cited

U.S. PATENT DOCUMENTS 5,700,782 * 12/1997 Cope et al. ........................... 426/656

OTHER PUBLICATIONS

Slavin, Joanne, *Nutritional benefits of soy protein and soy fiber*, Journal of the American Dietetic Association, vol. 91, No. 7, pp. 816–819, Jul. 1991.

Brewer, et al., *Effect of Soy Protein Isolate and Soy Fiber on Color, Physical and Sensory Characteristics of Baked Products*, Journal of Food Quality, vol. 15, pp. 245–262, 1992.

Protein Technologies International, *Soy bean renaissance*, Food Industry News, pp. 12–13, Feb. 1995.

Potter, et al., *Depression of plasma cholesterol in men by consumption of baked products containing soy protein*, Am. J. Clin. Nutr., vol. 58, pp. 501–506, 1993.

Bakhit, et al., *Intake of 25 g of Soybean Protein with or without Soybean Fiber Alters Plasma Lipids in Men with Elevated Cholesterol Concentrations*, J. Nutr. vol. 124, pp. 213–222, 1994.

Basler H.—D. et al., *Nicotine gum assisted group therapy in smokers with an increased risk of coronary disease evaluation in primary care setting format*, Health Educ. Res., vol. 7. No. 1, pp. 87–95, 1992.

Shapiro, Florrey et al., *Smoking Cessation And Severity of Weight Gain (Corresponding)*, The New Englang Journal of Medicine, vol. 325, No. 7, pp. 517–518, 1991.

Nides M. et al., *Weight gain as a function of smoking cessation and 2—mg nicotine gum use among middle aged smokers with mild lung impairment in the first 2 years of the Lung Heath Study*, Health Phychol, vol. 13, No. 4. pp. 354–361, Jul. 1994.

Gross J. et al., *Nicotine replacement ten–week effects of tobacco withdrawal symptoms*, Physopharmacology, vol. 98, No. 3, pp. 334–341, 1989.

* cited by examiner

Primary Examiner—Anthony J. Weier
(74) Attorney, Agent, or Firm—Iver P. Cooper

(57) ABSTRACT

A composition on basis of soybean ingredients contains (a) isolated soy protein, (b) soybean fibres, and optionally an additional protein source, a carbohydrate source, a fat source, flavouring agents, vitamins, minerals, electrolytes, trace elements and other conventional additives, the amount of (a) being such that the protein content provides at least 15% of the total energy content of the composition, and (I) the weight ratio of (a) to (b) is at least 2 and (a) is at least 75 wt % of the total protein content, or (II) the ratio of (a) to (b) is at least 3. The composition is useful as partial or total diet for overweight or obese subjects and is furthermore useful for lowering the cholesterol level and the triglyceride level and for increasing the HDL/LDL-cholesterol ratio in serum.

13 Claims, No Drawings

COMPOSITION AND ITS USE AS A FOOD SUPPLEMENT OR FOR LOWERING LIPIDS IN SERUM

This is a continuation of parent application Ser. No. 09/143,120 filed Aug. 28, 1998, now U.S. Pat. No. 6,136,367, continuation of PCT/IB97/00152, filed Feb. 12, 1997.

The present invention relates to a composition on basis of soybean ingredients. More particularly, the invention relates to a nutritional composition which is useful as a weight-reducing diet for overweight or obese subjects. Furthermore, the invention relates to such a nutritional composition, which is useful for lowering serum lipids Adipositas or obesity and overweight in general is a widespread problem in large parts of the world. At the same time, increased health consciousness has stimulated the interest in "keeping the slim line". A large number of different diets have therefore been put on the market aiming at a rapid weight reduction.

Some of these diets must be considered unwarrantable seen from a nutritional point of view as they are based on a very unbalanced intake of nutrients which very quickly will result in deficiency of essential nutrients.

Other diets are based on nutritional preparations being composed in such a way that, at a low calorie content, they supply the necessary proteins, vitamins and minerals. Some of these preparations are in the form of powders containing sources of protein, carbohydrate and fat, and optionally flavouring agents, preservatives, vitamins, minerals and other conventional additives. Before intake, the powders are stirred up in water and then taken as a drink or a gruel. However, the known preparations suffer from a number of deficiencies. Many known powders can only with difficulty be stirred up in water so that the stirred up preparations will have a lumpy and gritty consistency which makes them very unpleasant to take. At the same time, sedimentation occurs very quickly, involving the risk that essential components such as sparingly soluble minerals are not taken in, but remain as a sediment at the bottom of the glass. Finally the preparations have an unpleasant tang which persists as an after-taste a long time after the preparation has been taken. These disadvantages have the effect that many persons break off the diet too soon.

EP0 425 423 B1 discloses a process for the preparation of a powdery, low-calorie nutritional preparation, especially for use as the main or sole nutrition in the treatment of adipositas. The preparation has a balanced composition of sources of protein, carbohydrate and fat, and optionally contains flavouring agents, preservatives, vitamins, minerals and other conventional additives. The protein source is a combination of a soy protein concentrate and skimmed milk powder. The soy protein concentrate is a product prepared from shelled soybeans by removing most of the oil and water soluble, non-protein constituents. Soy protein concentrate typically contains 66.0% protein, 17.0% carbohydrate, 6.0% water, 5.6% ashes, 4.0% wood substance, and 1.4% fat. The carbohydrate content is typically present as fibres which are insoluble in water. A typical soy protein concentrate does not contain all the essential amino acids in sufficient amounts. In particular, histidine and tryptophan are limiting amino acids in soy protein concentrate. In order to supply all the essential amino acids, the known nutritional preparation also contains skimmed milk powder as a protein source. However, skimmed milk is not a desirable protein source in certain parts of the world, in particular Southern Europe, Asia and Africa where lactose intolerance is not unusual due to lack of the lactose-degrading enzyme, lactase. Overweight and obesity are often accompanied by an increased fatty content in the blood, and for altering the lipid profile EP-0 425 423 B1 suggests supply of separate capsules comprising fish oil containing polyunsaturated fatty acids along with the nutritional preparation. It would be desirable if the intake of separate fish oil capsules could be avoided for improving the lipid profile. Thus, it would be highly desirable to provide a nutritional preparation which in itself had a beneficial lowering effect upon the lipid level.

As mentioned above, some of the diets presently on the market for weight reduction are based on an unbalanced intake of nutrients, which may result in deficiency of essential nutrients. In particular, a sufficient intake of protein supplying all the essential amino acids is very important in connection with any weight reducing treatment. Typically, 22–36% of the overweight is lean body mass (LBM), which is the fat-free body mass, such as musculature. The loss of proteins from e.g. muscles results in elimination of nitrogen from the body, which can be measured indirectly by determination of the concentration of uric acid in serum. If the concentration of uric acid increases substantially during a weight reduction, the reason may be too much degradation of musculature.

In New England Journal of Medicine, Vol. 333, Aug. 3, 1995, a meta-analysis of the effects of soy protein intake on serum lipids, has been described. In this study, the authors examined the relation between soy protein consumption and serum lipid concentrations in humans. It was found that ingestion of diets containing soy protein, as compared with control diets was accompanied by significant reduction in serum concentrations of total cholesterol, LDL-cholesterol and triglycerides. Soy protein intake did not significantly affect serum HDL cholesterol concentrations. The effect of soy protein intake was dependent upon initial cholesterol concentration. Subjects with normal cholesterol levels had non-significant reductions of 3.3%, and also subjects with mild hypercholesterolemia had non-significant reductions of 4.4%. Only subjects with moderate and severe hypercholesterolemia had significant decreases in cholesterol levels of 7.4% and 19.6%, respectively. The pattern of changes in serum LDL-cholesterol concentrations was similar to the pattern for total cholesterol concentrations. Also changes in serum triglyceride concentrations were significantly related to the initial serum triglyceride concentrations. Various types of soy protein were studied, such as isolated soy protein, textured soy protein, or a combination, and it was found that the type of soy protein did not have any significant effect on the net change in serum cholesterol concentrations. The study did not consider a simultaneous intake of the various types of soy proteins along with soy fibres. This meta-analysis of the effects of soy protein intake on serum lipids found its way to the international press as a sensational finding that soy protein is effective in lowering serum cholesterol, and articles appeared in International Herald Tribune on Aug. 4, 1995, Chicago Tribune on Aug. 3, 1995, and in New York Times on Aug. 3, 1995.

Potter et al., Am J Nutr Clin 1993; 58; 501–6, studied the effects of soy protein consumption with and without soy fiber-on plasma lipids in mildly hyperchoesterolemic men. Dietary treatment included 50 g protein and 20 g dietary, fiber from soy flour, isolated soy protein/soy cotyledon fiber, isolated soy protein/cellulose, and non-fat dry milk/cellulose in conjunction with a low-fat, low-cholesterol diet. The protein and dietary fibres were prepared as baked products and substituted into the diet. In the experiment using isolated soy protein and soy cotyledon fiber the subjects received per day 50 g isolated soy protein, 50 g other proteins, including 36 g animal and 14 g vegetable protein, carbohydrates corresponding to 55% energy intake, 20 g soy cotyledon fiber, fat corresponding to <30% of total energy content, and 200 mg cholesterol. As a result of the study, it was found that total and LDL-cholesterol concentrations can be lowered significantly in mildly hypercholesterolemic men, which was attributed to the replacement of 50% of dietary protein with soy protein. Similar depressions in blood lipids were noted for isolated soy protein, whether it was consumed in conjunction with soy cotyledon fiber or cellulose fiber. Plasma triclycerides concentrations were unaffected by the various dietary treatments described in the article. The study did not reveal any additive cholesterol-lowering effect of concurrent intake of cotyledon soy fiber with isolated soy protein, and specifically the authors stated: "Whether or not there is an added benefit in lowering blood cholesterol concentrations from increased concurrent intake of soy protein and fiber in humans is not known."

Bakhit et al., J Nutr (in press) 1993, also studied mildly hypercholesterolemic men receiving a baseline diet in combination with four experimental treatments. For each dietary treatment, four types of muffins were prepared and baked, individually packaged, frozen and stored at −20° C. until distributed to subjects on a weekly basis. The four muffins containing appropriate test proteins and fibres were added to the basal diet replacing a total of 2.51 MJ of the subject's normal intake. The test proteins used were isolated soy protein and casein as sodium casenite. Fibres were soy cotyledon fibres and cellulose fibres. Protein and fiber were incorporated into the muffins to provide 25 g of protein and 20 g of dietary fiber daily in four muffins. The weight ratio between protein and fibres were in all cases 1.25, and the amount of protein corresponded to 20% of the total energy content. The coal of the study was to evaluate the ability of a relatively low level of soybean protein intake (25 g≈5% of energy intake per day) with and without soy cotyledon fibres, to decrease plasma lipid concentrations when consumed along with a typical low-lipid diet. As a result, it was found that addling of 25 g of soybean protein to a low-fat, low-cholesterol diet lowers total cholesterol concentrations in men with elevated blood lipids. In subjects having lower blood cholesterol concentrations (<5.7-mmol/l), this level of soybean protein intake did not influence blood lipids, and it was suggested that plasma lipids may even be elevated in some subjects following soybean ingestion. Also other previous studies have found that in general individuals with pre-existing hypercholesterolemia respond to soybean protein, whereas individuals with normal cholesterol values do not. Bakhit et al. did not observe an additive effect of concurrent ingestion of soybean protein and soybean fiber. According to the authors, soybean protein may affect cholesterol metabolism directly, possible via modulation of endocrine status, whereas soybean fiber most likely acts by interrupting enterohepatic circulation of bile.

In conclusion, the above-discussed studies of Potter et al. and Bakhit et al. did not find any serum lipid lowering effect in subjects having a normal blood cholesterol concentration below 5.7 mmol/l.

High serum levels of cholesterol cause disease and death by contributing to the formation of atherosclerotic plaques in arteries throughout the body. In order to reduce high serum cholesterol levels, subjects may be put on a low fat, low cholesterol diet or may be treated with medicaments such as statins, or a combination of both. The statins selectively inhibit HMG-CoA-reductase which is the controlling enzyme in the cholesterol synthesis. The enzyme increases the formation of LDL receptors and among other hereby decreases the level of LDL-cholesterol in the blood. Once the serum level of cholesterol has been lowered to a normal value, it will be desirable to avoid further medication by subjecting the individual to a diet which can retain serum levels of cholesterol at a normal value and more preferably lower the serum cholesterol concentration below a value of 5.7 mmol/l. Also many physicians find that a serum cholesterol level of 5.7 mmol/l is too high, especially in subjects with a history of cardiovascular disease, where it is medically proven that a lower cholesterol level than 5.7 mmol/l reduces myocardial infarction and deaths considerably. Thus, there is a need for a composition which can lower serum cholesterol concentrations in subjects having a normal serum lipid concentration.

It has now surprisingly been found that serum lipid concentrations in subjects having normal serum lipid concentrations are significantly lowered by intake of a composition according to the present invention on basis of a particular combination of soy bean ingredients. As a further benefit, the composition of the present invention not only lowers normal serum lipid concentrations, but it also has a lipid-lowering effect in subjects having increased serum lipid concentrations. The lipid-lowering effect is more-pronounced the higher the initial value. It has also been found that the composition of the invention can lower the level of cholesterol and triglycerides in subjects who have been treated with cholesterol lowering medications such as statins. Furthermore, it has been found that a composition of the present invention can lower the serum cholesterol level in a hypercholesterolemic patient whose cholesterol level has been partly lowered by a diet with a low fat and calorie intake, recommended by doctors.

A composition according to the present invention has been found to reduce the level of total cholesterol and total triglycerides. The HDL/LDL-cholesterol ratio in serum is also improved. Also, it has been found that the lipid-reducing activity of such a composition can be increased by adding increasing amounts of isolated soy protein, carbohydrate and fat to the composition. It is particularly surprising that increasing amounts of fat may lower serum lipid concentrations as it is well known that the amount of fat in food is considered to be responsible for increased cholesterol and triglyceride levels. As a further surprising feature it has been found that the increase in uric acid concentration is lowered when the compositions are used as a total diet. Therefore, a nutritional composition in accordance with the present invention is very useful as a nutritional composition in a weight reduction treatment for overweight or obese subjects, who very often have increased levels of triglycerides and are at risk of having hypercholesterolemia. Furthermore, a nutritional composition in accordance with the present invention will be useful as a nutraceutical, i.e. a nutritional composition used as a pharmaceutical. In this aspect, the composition is a medicament based upon naturally occurring raw materials for lowering the blood cholesterol and triglyceride levels and for increasing the HDL/LDL-cholesterol ratio in serum.

In a first aspect of the present invention, there is provided a nutritional composition on basis of soybean ingredients comprising
  (a) isolated soy protein
  (b) soybean fibres, and
    optionally an additional protein source, a carbohydrate source, a fat source, flavouring agents, vitamins, minerals, electrolytes, trace elements and other conventional additives,
the amount of (a) being such that the protein content provides at least 15% of the total energy content of the composition, and the weight ratio between (a) and (b) being at least 2. Preferably, the weight ratio between (a) and (b) is at least 2.5 and more preferably the ratio is at least 3 with the most preferred value being between 3 and 4.

Isolated soy protein is the major proteinatious fraction of soybeans. It is prepared from high quality, sound, cleaned, dehulled soybeans by removing a preponderance of the non-protein components which shall contain not less than 90% protein (N×6.25) on a moisture free basis. The preparation takes place through a series of steps in which the soybean protein portion is separated from the rest of the soybean. The removal of carbohydrate results in a product which is essentially bland in flavour and therefore useful in a nutritional composition for humans. The isolated soy protein used in the composition of the present invention should preferably supply all the essential amino acids in the amounts required for humans. Preferably, the isolated soy protein should meet or exceed the essential amino acid requirement pattern for children and adults as established by the Food and Agricultural Organisation, World Health Organisation and United Nations University (FAO/WHO, UNU). Also the preferred isolated soy protein should be highly digestible, comparable in digestibility to milk, meat, fish and egg protein. Finally, the preferred isolated soy protein shall be effective in maintaining nitrogen balance when consumed at the recommended protein intake level. Preferred isolated soy protein products which meet the foregoing requirements are supplied by Protein Technologies International under the brand name SUPRO®. SUPRO® isolated soy proteins are supplied in many different qualities. One particularly preferred product is SUPRO PLUS® 2100, which is a protein product consisting of isolated soy protein, sweet diary whey and calcium phosphate. It offers excellent nutritional properties, a bland flavour and smooth mouthfeel. It is spray-dried to provide excellent dispersibility and suspension properties, and it is particularly recommended for dry blended beverages designed to be mixed with water, juice or milk. Another particularly preferred isolated soy protein product is SUPRO® 661, which is a protein which offers excellent dispersibility, bland flavour and excellent nutritional properties. It has a high bulk density and is therefore recommended for dry blended applications requiring a high density protein source to achieve certain can fill requirements.

Preferably, the isolated soy protein is the main or sole protein source in a nutritional composition according to the present invention. However, parts of the protein source may be provided by other proteins such as soy protein concentrate, skimmed milk, preferably as a powder, and other vegetable or animal, including diary, proteins. Preferably, at least 90 weight % of the protein source is isolated soy protein, and less preferred at least 50% of the protein source is isolated soy protein.

The soybean fibres used in the nutritional composition of the present invention are fibres which may be isolated from soybeans in a number of different ways. One available source would be soy protein concentrate, as discussed above. Preferably, the soybean fibres are isolated from the cotyledon of soybeans. In particular, such fibres are derived from dehulled and defatted soybean cotyledon and are comprised of a mixture of cellulosic and non-cellulosic internal cell-wall structural components. Such fibres are distinctly different from soy fibes derived from soy hulls as well as other fiber sources. Soy cotyledon fibres are bland-tasting, contain no cholesterol and are low in fat and sodium. They have good water-binding properties and low caloric content, which make them ideal as bulking agents. Soy cotyledon fibres supplied in a fat-modified and low-cholesterol diet have been found to further reduce blood cholesterol level in subjects with elevated plasma cholesterol levels. The effect is a lowering of sternum total cholesterol and a lowering of LDL-cholesterol. HDL-cholesterol and total triglycerides are not significantly affected by soy cotyledon fibres. In the present invention, soybean fibres, in particular from the cotyledon of soybeans, are believed to provide a synergistic effect in combination with isolated soy protein so as to lower lipid concentration in subjects both having normal and elevated concentrations of total cholesterol and total triglycerides. The amount of soybean fibres shall be a maximum of 50 weight % of the isolated soy protein, and preferred amounts are between 25 and 33 weight %. The amount of soybean fibres is preferably at least 5 weight % of the total weight of the nutritional composition on a dry basis. The preferred daily dosage, when the nutritional composition of the invention is used as a total diet, is 20–30 g soybean fibres. A particularly preferred soy cotyledon fiber product is manufactured by Protein Technologies International under the trademark FIBRIM®, and among the various soy fibres produced under the FIBRIM® brand, FIBRIM® 1020 is preferred according to the present invention because it has a particularly good mouthfeel and dispersibility for dry blended beverage applications As mentioned above, isolated soy protein is preferably the main- or sole source of protein, but other proteins may be present. The protein content should provide at least 15% of the total energy content of the composition. More preferred, the protein provides at least 20%, preferably at least 25% and more preferred at least 30% of the total energy content of the composition. In terms of weight, it is preferred that the isolated soy protein amounts to no less than 50 weighty %, preferably no less than 75 weight %, and more preferred no less than 90 weight %, of the total protein content of the composition. Such weight proportions of protein are much higher than in the diets studied by Potter et al. (loc cit) and Bakhit et al. (loc sit).

A composition according to the present invention may optionally comprise a carbohydrate source, a fat source, flavouring agents, vitamins, minerals, electrolytes, trace elements and other conventional additives. If any of these optional ingredients are not present in the composition of the invention, they should normally be supplied as a supplement to the nutritional composition of the invention, so that an adequate supply of all essential nutritional ingredients is ensured. If the composition of the invention is intended to supply a substantial part of the food intake of a subject, the optional ingredients are preferably present, so that separate intake thereof can be avoided. This is of particular importance for overweight or obese subjects on a weight reduction treatment, by which it is important that all essential nutritional ingredients are supplied in recommended amounts.

When a carbohydrate source is present in the composition, it is preferably present in an amount of less than 50 weight % of the composition. Preferably the amount of carbohydrate amounts to at least 20 weight %, more preferred at least 25 weight %, and most preferred at least 30 weight %, of the composition.

The preferred carbohydrates for use in the invention are glucose, fructose and for maltodextrine. Skimmed milk and cocoa are other possible carbohydrate sources.

When a fat source is present in the composition of the invention, it is usually present in an amount from 3 to 50 weight %, preferably 4 to 40 weight %, more preferably from 4 to 12 weight %, and most preferably from 5 to 10 weight %. of the composition. The fat source will preferably comprise polyunsaturated fatty acids and monounsaturated fatty acids as well as saturated fatty acids. The amount of polyunsaturated fatty acids and monounsaturated fatty acids, including the essential fatty acids, may range from 35 to 50, preferably 38 to 44, weight % of the total amount of the fat source. The essential fatty acids are also called omega-6 and omega-3 fatty acids and include linolic acid and linolenic acid. The amount of saturated fatty acids may be from 20 to 30 weight %, preferably 22 to 26 weight %, of the total amount of fat.

Normally, the nutritional composition of the invention will also comprise one or more flavouring agents such as cocoa, vanilla, lime, strawberry or soup flavours, such as mushroom, tomato or bouillon.

Vitamins and minerals will be added to the composition in accordance with the limits laid down by health authorities. Preferably, the composition of the invention will comprise all recommended vitamins and minerals. The vitamins will typically include A, B1, B2, B12, folic acid, niacin, panthotenic acid, biotin, C, D, E and K. The minerals will typically include iron, zink,iodine, cobber, manganese, chromium and selenium. Electrolytes, such as sodium, potassium and chlorides, trace elements and other conventional additives are also added in recommended amounts.

The composition of the invention may take any form which is suitable for human consumption. In a preferred embodiment, the composition is a powdery mixture which is suspendable, dispersible or emulsifiable in a water-containing liquid such as water, coffee, tea or fruit juice. For such purpose, the composition is preferably packed in a package intended for covering the total nutrition requirement for a defined period of time, such as three days or a week, whereby the composition will be divided into suitable sub-units of a daily dose, preferably four to five sub-units for women and four to six sub-units for men per daily dosage, which are packed separately before being packed into the package, or the package will be provided with means for a portioning of such sub-units.

In another preferred embodiment, the composition of the invention is a liquid nutritional preparation in a water-containing liquid, in which the solid ingredients are suspended, dispersed or emulgated in an amount of 10 to 25 weight , When the liquid nutritional preparation is intended for drinking, it will usually comprise a flavouring agent as discussed above. However, the liquid nutritional preparation may also be used for intravenous administration or for probe administration.

In a further embodiment, the nutritional composition of the invention may be in the form of a solid composition such as a nutritional bar, fruit bar, cookie, cake, bread or muffin.

In another aspect, the invention relates to the use of a composition according to the invention as partial or total diet for overweight or. obese subjects. Overweight or obese persons often have an increased serum cholesterol level and an increased triglyceride level, and the composition of the invention will have the effect of lowering these variables. Very surprisingly, the composition of the invention also has a substantial lowering effect on total serum cholesterol level and total triglyceride level in persons having a normal lipid profile. For the purpose of the present invention, subjects having an initial total serum cholesterol level of 5.7 mmol/l or below are considered to have a normal or hypocholesterolemic level, whereas subjects having a total serum cholesterol level above 5.7 mmol/l are considered to be hypercholesterolemic. It is believed that a significant lipid-lowering effect on subjects having a normal serum cholesterol level has not previously been observed as a result of treatment with a composition on basis of soybean ingredients comprising isolated soy protein and soybean fibres such as soy cotyledon fibres. Therefore, in a further aspect, the invention provides for the use of a composition according to the invention as a medicament for lowering the blood cholesterol level and the triglyceride level, and for increasing the HDL/LDL-cholesterol ratio in serum. The medical use of the composition according to the invention is not limited to overweight or obese subjects, but may also be used for normal weight subjects having increased serum cholesterol level. As mentioned previously, the composition according to the invention also has a lowering effect upon the increase in uric acid concentration normally found in weight reduction treatments where protein may be degradated from the fat-free body mass, e.g. the musculature. Therefore, a composition according to the invention provides for increased safety if used as a total meal replacement.

A composition according to the invention may also be used as a partial meal replacement for lowering cholesterol in hypercholesterolemic patients. For example, one to three daily meals of ordinary food can be replaced by a composition according to the present invention. Hereby, significant cholesterol and triglyceride reductions can be obtained, as well as improvement of HDL/LDL cholesterol ratio.

For use in a weight loss treatment, the daily dose of the composition of the invention may comprise an energy content from 400 to 800, in particular from 450 to 800 kcal/day, which is considered to be a very low calorie diet (VLCD), or it may comprise from 800 to 1200 kcal/day, which is considered to be a low-calorie diet (LCD). In the medical aspect of the invention, the energy content may correspond to the daily energy requirement of a normal person, or the composition can be used as an emergency ration in isolated areas, in which case the energy content may correspond to 2000–2500 kcal/day.

The composition of the present invention will also be useful in an anti-smoking programmed to avoid weight gain after smoking cessation. For such a purpose, a composition according to the present invention may be used in combination with a nicotine substitution such as nicotine chewing gum or a corresponding nicotine patch. Since use of a composition according to the present invention may counteract a weight gain, smokers may hereby become more motivated for quitting tobacco with a possibly higher success rate in smoking cessation The invention will be further illustrated in the following, non-limiting examples.

EXAMPLE 1

The following ingredients were mixed:

| | |
|---|---|
| Isolated soy protein | 60 g |
| Fat | 8 g |
| Carbohydrate | 50 g |
| Soy fiber | 20 g |
| Vitamins, minerals, electrolytes and trace elements, approximately | 5 g |

The mixture was suspended in approximately 1000 ml water to provide a drink comprising about 530 kcal, corresponding to the daily dosage for a VLCD preparation.

EXAMPLE 2

The following ingredients were mixed:

| | |
|---|---|
| Isolated soy protein | 75 g |
| Fat | 22 g |
| Carbohydrate | 100 g |
| Soy fiber | 20 g |
| Vitamins, minerals, electrolytes and trace elements, approximately | 5 g |

The mixture was suspended in approximately 1000 ml water to provide a drink comprising about 880 kcal, corresponding to the daily dosage for a LCD preparation.

EXAMPLE 3

The products of examples 1 and 2 were investigated in a clinical trial at Karolinska Hospital, Stockholm, Sweden.

The number of patients needed in each treatment group was calculated to 27 in order to detect a true treatment difference of 4 kg between the treatment groups VLCD/530 and LCD/880, using an estimate of the standard deviation of 12, using a significance level of 5%/3=1.7% and a power of 80%.

The patients were selected according to the following inclusion criteria:

Moderate to severe overweight persons with body mass index (BMI) <30 kg/rM$^2$ both sexes age between 20 and 65 a self-reported, stable body weight within the last two months.

TABLE 1

Description of age (years).

| Treatment | N | Mean | SD | Min | Max |
|---|---|---|---|---|---|
| 530 kcal/day | 32 | 40.84 | 12.54 | 22 | 65 |
| 880 kcal/day | 31 | 39.39 | 10.15 | 24 | 65 |

TABLE 2

Description of sex distribution.

| Sex | 530 kcal/day | 880 kcal/day |
|---|---|---|
| Male | 10 | 10 |
| Female | 22 | 21 |

TABLE 3

Description of body mass index (kg/m$^2$)

| Treatment | N | Mean | SD | Min | Max |
|---|---|---|---|---|---|
| 530 kcal/day | 32 | 39.0 | 5.2 | 33.0 | 60.56 |
| 880 kcal/day | 31 | 38.4 | 4.3 | 32.5 | 50.7 |

WEIGHT

The weight was recorded at every visit for the subjects in all three groups. The weight is described below.

TABLE 4

Description of weight (kg).

| | 530 kcal/day | | | | | 880 kcal/day | | | | |
|---|---|---|---|---|---|---|---|---|---|---|
| Week | N | Mean | SD | Min | Max | N | Mean | SD | Min | Max |
| 0 | 32 | 113.8 | 18.0 | 81.0 | 158.9 | 31 | 113.8 | 18.7 | 85.6 | 157.1 |
| 6 | 28 | 99.0 | 15.5 | 72.7 | 127.9 | 29 | 103.1 | 15.6 | 80.1 | 136.7 |

TABLE 5

Description of cholesterol (mmol/l)

| | 530 kcal/day | | | | | 880 kcal/day | | | | |
|---|---|---|---|---|---|---|---|---|---|---|
| Week | N | Mean | SD | Min | Max | N | Mean | SD | Min | Max |
| 0 | 32 | 5.6 | 1.0 | 3.6 | 8.0 | 31 | 5.6 | 1.0 | 3.5 | 7.4 |
| 6 | 28 | 4.2 | 0.8 | 3.1 | 5.8 | 29 | 4.1 | 0.7 | 2.8 | 5.4 |

From the above table, it can be calculated that VLCD/530 provided a cholesterol reduction of 25% in six weeks, and LCD/880 provided a cholesterol reduction of 26.8% in six weeks. In VLCD/530 the daily fat intake. was 8 g, and in LCD/880 it was 22 g. The initial cholesterol level of 5.6 mmol/ in both treatment groups corresponds to a normal cholesterol level, and as can be noted there is a significant reduction of cholesterol after six weeks, which is higher when the intake of fat, carbohydrate and soy protein is increased.

TABLE 6

Description of triglycerides (mmol/l)

| | 530 kcal/day | | | | | 880 kcal/day | | | | |
|---|---|---|---|---|---|---|---|---|---|---|
| Week | N | Mean | SD | Min | Max | N | Mean | SD | Min | Max |
| 0 | 32 | 2.0 | 1.1 | 0.8 | 5.9 | 31 | 1.8 | 1.0 | 0.7 | 4.5 |
| 6 | 28 | 1.4 | 0.5 | 0.7 | 3.1 | 27 | 1.0 | 0.3 | 0.8 | 2.3 |

From the values in the table it can be calculated that the triglyceride concentration was lowered by 30% in the group receiving the LCD/530, and 44,5% in the group receiving LCD 880. Again it can-be seen that the reduction of triglyceride concentration was highest in the group receiving most fat, carbohydrate and isolated soy protein.

TABLE 7

Description of uric acid ($\mu$mol/l).

| | 530 kcal/day | | | | | 880 kcal/day | | | | |
|---|---|---|---|---|---|---|---|---|---|---|
| Week | N | Mean | SD | Min | Max | N | Mean | SD | Min | Max |
| 0 | 32 | 338.3 | 66.8 | 182 | 466 | 30 | 316.2 | 78.8 | 109 | 457 |
| 6 | 28 | 413.1 | 118.3 | 148 | 803 | 29 | 364.3 | 111.4 | 73 | 539 |

From the table it can be calculated that uric acid concentration increased by 35 22.1% in the group receiving the LCD/530 and by 15.2% in the group receiving the LCD/880. In a comparative study with a VLCD/420 product prepared according to EP-0 425 423 B1 and which contained soybean concentrate with fibres, the uric acid concentration increased by 27.9% in the same six week period.

EXAMPLE 4 (COMPARISON)

A nutrition powder prepared according to EP-0 425 423 B1 is concentrically available under the trademark NUTRILETT® VLCD 420. This composition provides 420 kcal per day and comprises 61.5 g protein as a combination of soy protein concentrate and skimmed milk powder, 6.0 g fat, including 2.0 g poly-unsaturated fat, 30.5 g carbohydrates and 17.5 g fibres derived from soy protein concentrate. The product is supplied with a fish oil capsule containing essential omega-3 fatty acids and a tablet containing Nordic Recommended Daily Allowances (RDA) of the vitamins, minerals and trace elements which do not occur sufficiently in the nutrition powder. VLCD 420 was compared with the products of Example 1 (VLCD 530) and Example 2 (LCD 880) and the results are shown in Tables I and II below.

in contrast to 22 g fat per clay for the composition of the present invention. Furthermore it can be seen that patients having a higher initial cholesterol value obtains a higher cholesterol lowering effect. For example the cholesterol lowering for men treated six weeks with the LCD 880, and having an initial cholesterol value of 6.25, was 32.8%.

EXAMPLE 5 (COMPARISON)

In another study NUTRILETT® VLCD 420 with the composition stated in Example 4 was given to a population of 152 females and 101 males, aged 15–72 years (median 41.6). Their body weight ranged from 70–177 kg (median 99.7) and body mass index (BME) from 25–51 kg/m2 (median 33.2). The patients were mildly hypercholesterolemic having an average total cholesterol of 6,0 mmol/l, and it was found that the mean total cholesterol level was lowered to 4.8 mmol/l after eight weeks of treatment with the preparation. In the same eight weeks' period the concentration of triglycerides was lowered from 3.1 mmol/l to 1.2 mmol/l.

TABLE I

DESCRIPTION OF CHOLESTEROL VALUE AT WEEK 0

| RECEIVED TREATMENT | CHOLESTEROL VALUE AT STUDY START | SEX | CHOLESTEROL VALUE AT WEEK 0 | | | |
|---|---|---|---|---|---|---|
| | | | N | MEAN | STD | MIN | MAX |
| VLCO 420 KCAL | <5 mmol/l | MALE | 1 | 4.80 | | 4.80 | 4.80 |
| | | FEMALE | 4 | 4.50 | 0.38 | 4.00 | 4.80 |
| | >5 mmol/l | MALE | 9 | 5.86 | 0.73 | 5.00 | 6.80 |
| | | FEMALE | 15 | 5.83 | 0.72 | 5.00 | 7.00 |
| VLCD 530 KCAL, 6W | <5 mmol/l | MALE | 2 | 4.85 | 0.21 | 4.50 | 4.80 |
| | | FEMALE | 5 | 4.18 | 0.37 | 3.60 | 4.60 |
| | >5 mmol/l | MALE | 8 | 6.01 | 1.02 | 5.00 | 8.00 |
| | | FEMALE | 17 | 5.89 | 0.62 | 5.00 | 7.50 |
| LCD 880 KCAL | <5 mmol/l | MALE | 2 | 4.60 | 0.28 | 4.40 | 4.80 |
| | | FEMALE | 8 | 4.40 | 0.47 | 3.50 | 4.90 |
| | >5 mmol/l | MALE | 8 | 6.25 | 0.68 | 5.30 | 7.20 |
| | | FEMALE | 13 | 5.97 | 0.66 | 5.20 | 7.40 |

TABLE II

DESCRIPTION OF CHOLESTEROL REDUCTION FROM WEEK 0 TO WEEK 6

| RECEIVED TREATMENT | CHOLESTEROL VALUE AT STUDY START | SEX | CHANGE IN CHOLESTEROL W 0–6 | | | |
|---|---|---|---|---|---|---|
| | | | N | MEAN | STD | MIN | MAX |
| VLCO 420 KCAL | <5 mmol/l | MALE | 1 | 1.40 | | 1.40 | 1.40 |
| | | FEMALE | 4 | 0.65 | 0.67 | 0.30 | 1.20 |
| | >5 mmol/l | MALE | 9 | 1.50 | 0.92 | 0.30 | 2.80 |
| | | FEMALE | 14 | 1.13 | 0.56 | 0.10 | 2.00 |
| VLCD 530 KCAL, 6W | <5 mmol/l | MALE | 2 | 1.05 | 0.49 | 0.70 | 1.40 |
| | | FEMALE | 3 | 1.00 | 0.25 | 0.70 | 1.20 |
| | >5 mmol/l | MALE | 8 | 1.73 | 0.96 | 0.40 | 3.40 |
| | | FEMALE | 15 | 1.51 | 0.73 | −0.10 | 2.40 |
| LCD 880 KCAL | <5 mmol/l | MALE | 2 | 0.95 | 0.35 | 0.70 | 1.20 |
| | | FEMALE | 7 | 0.83 | 0.83 | −0.40 | 1.80 |
| | >5 mmol/l | MALE | 8 | 2.05 | 0.73 | 1.00 | 3.20 |
| | | FEMALE | 12 | 1.34 | 0.82 | −0.20 | 3.20 |

From the results of table I and table II it can be concluded that the VLCID 530 lowers cholesterol by 25% and LCD 880 lowers cholesterol by 27% during six weeks treatment. The LCD 880 is thereby more than 20% more effective regarding cholesterol reduction than the previous VLCD 420 product even though the latter only provides 6 g fat per day The reduction in average total cholesterol from 6.0 mmol/l to 4.8 mmol/l in mildly hypercholesterolemic patients corresponds to 20%.

EXAMPLE 6

A hypercholesterolemic patient was treated with Zocor® (one of the statins) whereby the serum cholesterol level was reduced to 6 mmol/l. Subsequently, the patient replaced his evening meal during one month by the LCD 880 preparation according to the present invention, whereby the cholesterol level was further reduced to 5.3 mmol/l (=12% reduction) and the triglyceride level was reduced from 2.66 to 2.15 mmol/l (=19% reduction). This shows that a further reduction in cholesterol and triglycerides may be obtained by a composition according to the present invention for a patient who has already been treated with a cholesterol lowering medicament.

EXAMPLE 7

A patient reduced the cholesterol level from 10 mmol/l to 8.3 mmol/l by means of a medical diet with a reduced fat and calorie intake. By replacing two daily meals with the LCD 880 according to the present invention, the cholesterol level was further reduced to 6.5 mmol/l during a three months period. This is a 22% reduction in comparison with the cholesterol level which was possible with the medically recommended diet.

What is claimed is:

1. A composition comprising:
   (a) isolated soy protein; and
   (b) soybean fibers;
   the weight of (a) and the weight of (b) being in a predetermined weight ratio;
      wherein the composition has a total protein content and a total energy content such that the total protein content provides at least 15% of the total energy content, and where
         (I) the weight ratio of (a) to (b) is at least 2, and the isolated soy protein is present in an amount of at least 75 weight percent of the total protein content of the composition, or
         (II) the weight ratio of (a) to (b) is at least 3, and the isolated soy protein is present in an amount of at least 50 weight percent of the total protein content of the composition, or
         (III) the weight ratio of (a) to (b) is in the range of 3 to 4.

2. The composition of claim 1 where clause (I) applies.
3. The composition of claim 1 where clause (II) applies.
4. The composition of claim 1 where clause (III) applies.
5. The composition of claim 1 in which the weight ratio of (a) to (b) is at least 3.
6. The composition according to claim 2 wherein isolated soy protein is present in an amount of at least 50 weight percent of the total protein content of the composition.
7. The composition according to claim 2 wherein isolated soy protein is present in an amount of at least 75 weight percent of the total protein content of the composition.
8. The composition according to claim 1 wherein isolated soy protein is present in an amount of at least 90 weight percent of the total protein content of the composition.
9. The composition according to claim 1 wherein substantially all of the protein is isolated soy protein.
10. A method of protecting a subject from an undsirable condition inhibitable by a composition comprising
   (a) isolated soy protein, and
   (b) soybean fibers;
      said method comprising administering to the subject an effective amount of said composition;
      the weight of (a) and the weight of (b) being in a predetermined weight ratio;
      wherein the composition has a total protein content and a total energy content such that the total protein content provides at least 15% of the total energy content;
      where
         (I) the weight ratio (a) to (b) is at least 2, and the isolated soy protein is present in an amount of at least 75 weight percent of the total protein content of the composition, or
         (II) the weight ratio of (a) to (b) is at least 3; and
      with the proviso that, if the subject is a person afflicted with cancer, said undesirable condition is not a nutritional need attributable to chemotherapy or radiation therapy for said cancer.

11. A method of protecting a subject from an undesirable condition inhibitable by a composition comprising
   (a) isolated soy protein, and
   (b) soybean fibers;
   said method comprising administering to the subject an effective amount of said composition;
      the weight of (a) and the weight of (b) being in a predetermined weight ratio;
      wherein the composition has a total protein content and a total energy content such that the total protein content provides at least 15% of the total energy content;
      where
         (I) (a) and (b) are in a weight ratio of at least 2, and the isolated soy protein is present in an amount of at least 75 weight percent of the total protein content of the composition, or
         (II) the weight ratio of (a) to (b) is at least 3; and
      where said subject is overweight or obese, is suffering from increased levels of serum triglycerides or serum cholesterol, or is a smoker.

12. A method of protecting a subject from an undesirable condition inhibitable by the composition of claim 1, said method comprising administering to the subject an effective amount of said composition,
   with the proviso that, if the subject is a person afflicted with cancer, said undesirable condition is not a nutritional need attributable to chemotherapy or radiation therapy for said cancer.

13. A method of protecting a subject from an undesirable condition inhibitable by the composition of claim 1, said method comprising administering to the subject an effective amount of said composition,
   where said subject is overweight or obese, is suffering from increased levels of serum triglycerides or serum cholesterol, or is a smoker.

* * * * *

UNITED STATES PATENT AND TRADEMARK OFFICE
CERTIFICATE OF CORRECTION

PATENT NO.    : 6,268,011 B1
DATED         : July 31, 2001
INVENTOR(S)   : Lars Henrik Hoie It is certified that error appears in the above-identified patent and that said Letters Patent is hereby corrected as shown below:

<u>Column 3,</u>
Line 34, delete "coal" and insert therefor -- goal --.
Line 39, delete "addling" and insert therefore -- adding --.

<u>Column 12,</u>
Line 12, delete "BME" and insert therefor -- BMI --.

Signed and Sealed this

Thirtieth Day of April, 2002

Attest:

JAMES E. ROGAN
*Attesting Officer*    *Director of the United States Patent and Trademark Office*